United States Patent [19]

Bartels

[11] 4,261,353

[45] Apr. 14, 1981

[54] HUMIDIFIER FILLER

[75] Inventor: Harold U. Bartels, Riverside, Calif.

[73] Assignee: Bourns Medical Systems, Inc., Riverside, Calif.

[21] Appl. No.: 68,117

[22] Filed: Aug. 20, 1979

[51] Int. Cl.³ .......................................... A61M 11/00
[52] U.S. Cl. ............................... 128/200.11; 220/254; 220/86 R; 215/355; 261/DIG. 65
[58] Field of Search ....................... 128/200.14, 200.16, 128/200.17, 200.18, 200.19, 200.21, 200.22, 200.23, 200.11, 200.13, 203.12, 203.16, 203.17, 204.11, 204.13; 220/254, 361, 375, 85 F, 86 R, DIG. 19; 261/DIG. 65, 72 R; 141/331–345; 215/309, 355

[56] References Cited

U.S. PATENT DOCUMENTS

| 1,320,559 | 11/1919 | Lambert | 220/361 X |
|---|---|---|---|
| 1,426,846 | 8/1922 | Craig | 220/86 |
| 2,890,696 | 6/1959 | Morris | 128/200.13 |
| 3,690,317 | 9/1972 | Millman | 128/200.16 |
| 4,098,853 | 7/1978 | Brown et al. | 128/200.13 X |

FOREIGN PATENT DOCUMENTS

| 658036 | 5/1929 | France | 128/200.14 |
| 509593 | 7/1939 | United Kingdom | 128/203.17 |

Primary Examiner—Henry J. Recla
Attorney, Agent, or Firm—William G. Becker; George Jameson

[57] ABSTRACT

A refilling device incorporated into mechanical ventilator machines as used in medical systems wherein a funnel is incorporated into the molded cover of a humidifier chamber. A lower portion of the incorporated funnel when attached to the humidifier chamber, defines a high fluid level at its narrow cylindrical dimension while the upper, wide cone-like dimension is covered by being fitted with sealing filler cap.

2 Claims, 3 Drawing Figures

HUMIDIFIER FILLER

BACKGROUND OF THE INVENTION

1. Field of the Invention

This invention relates generally to humidifiers as used in medical respiratory apparatus and more particularly to means for refilling these devices with fluids.

2. Description of the Prior Art

Humidifiers are known in which refilling means are available, albeit with varying degrees of difficulty. Typically, refilling is accomplished by disconnecting one of the patient connecting tubes and pouring about 200 to 300 milliliters of fluid through the small tubular opening thereby exposed. The method is tedious, slow, inconvenient and often results in spillage to the detriment of system electronics and associated other equipment.

A novelty search conducted in the United States Patent and Trademark Office to locate patents relevant to the above topic did not disclose any patents contemplating a sealed humidifier refilling means for medical humidifiers as used in mechanical ventilator systems. Two patents dealing generally with refilling, however, were discovered. The following are, therefore, considered to be of potential interest:

| U.S. Pat. No. | Title | Inventor |
| --- | --- | --- |
| 2,164,881 | "Vaporizer" | L. B. Meyerson |
| 3,617,698 | "Vaporizer Apparatus" | R. H. Duncanson |

The fields of search were:

| | | |
| --- | --- | --- |
| Class 128 | Subclass | 186 |
| | | 192 |
| | | 193 |
| | | 194 |
| Class 261 | Digest | 65 |

It would thus be a great advantage to the art to provide a convenient means for adding to the fluid level in the humidifier means incorporated in a mechanical medical ventilator apparatus.

Another advantage to the art would be the facility to allow visual inspection of the fluid level while refilling or replenishing.

An additional advantage would be realized if such replenishment could be accomplished without disconnecting the humidifier from the system.

Still another advantage would be the provision for easy resealing of the humidifier system after refilling so as to exclude dust, bacteria and other contaminants.

SUMMARY OF THE INVENTION

In light of the advantages sought to be accomplished in the instant invention, it is thus an object of the present invention to provide a convenient means for adding to the fluid level in the humidifier means incorporated in a mechanical medical ventilator apparatus.

Another object of the instant invention is to provide the facility to allow visual inspection of the fluid level while refilling or replenishing the fluid in the humidifier.

An additional object is to provide means to accomplish replenishment of the humidifier fluid without disconnecting any of the connecting tubes in the system.

Still another object of the present invention is to provide easy resealing of the system of the humidifier system after refilling or replenishing so as to exclude dust, bacteria and other contaminants.

In the accomplishment of these and other objects, a sealable humidifier refill means is provided in which a funnel is incorporated into the molded cover of the humidifier chamber. The large end of the funnel accepts a sealing cap for the purpose of excluding contaminants. When the cap is removed, a relatively large area, i.e., the mouth of the funnel, is available to accept the fluid to be added to the system. It is thus possible, due to the large mouth of the funnel, to reduce spillage when adding fluid to the humidifier. The small part of the funnel terminates in the humidifier chamber at the high level water mark. Overfilling can thus be avoided by visual monitoring to ascertain when the fluid level reaches the bottom of the funnel. When sufficient fluid has been added to the system, the filler cap is then inserted in the funnel so as to seal the system from contaminants.

BRIEF DESCRIPTION OF THE DRAWINGS

Further advantages and features of the present invention will be more fully apparent to those skilled in the art to which the invention pertains from the ensuing detailed description thereof, regarded in conjuction with the accompanying drawings wherein like reference characters refer to like parts throughout and in which.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obivous to one skilled in the art to which the invention pertains are deemed to be within the spirit, scope and contemplation of the invention as further defined in the appended claims.

Figure 1:
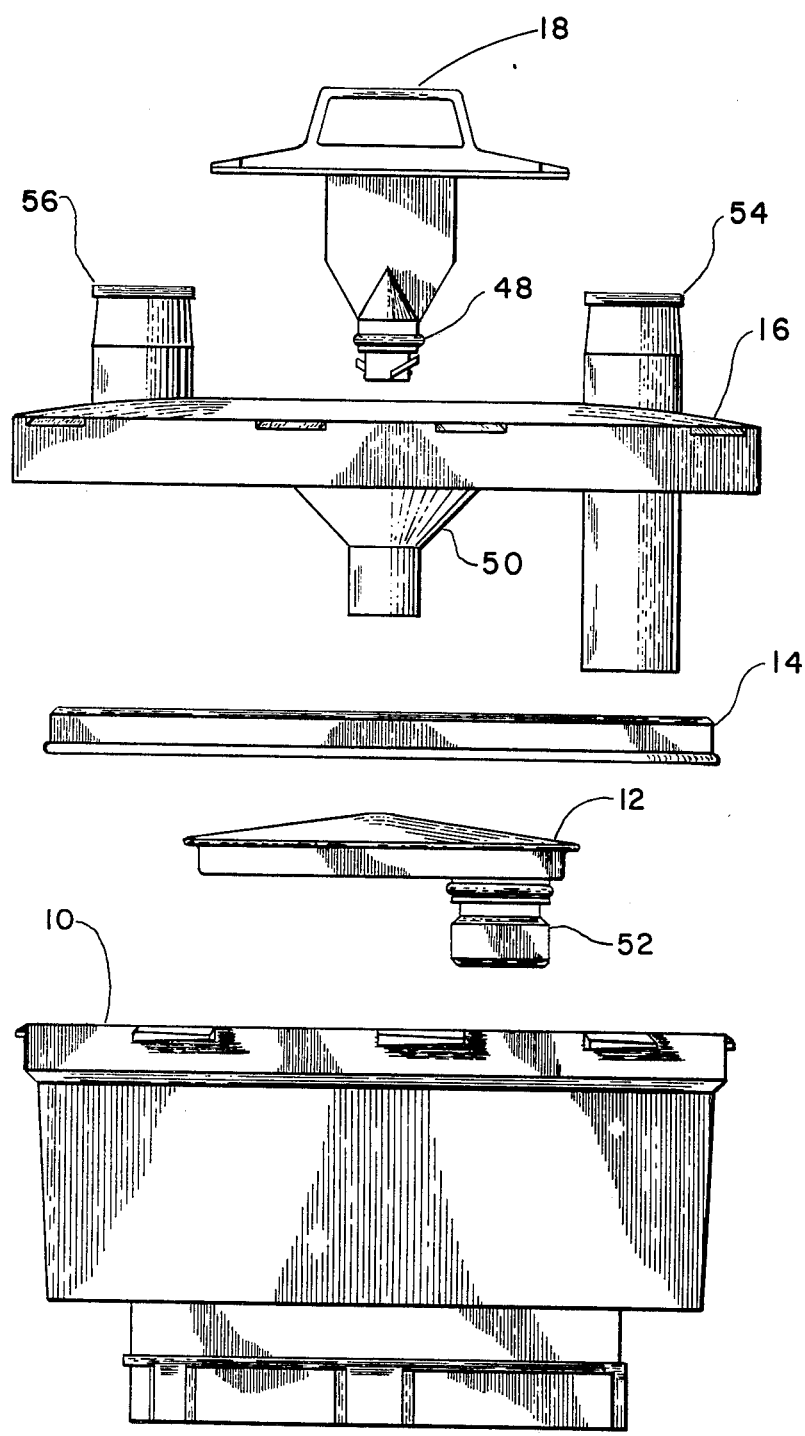
FIG. 1 is an idealized conceptualized drawing showing the principal elements of a humidifier system.

Referring to FIG. 1 with greater particularity, a system in which the present invention might be utilized is illustrated. The basic jar assembly 10 accepts a heater assembly 12 having a connector assembly 52. A lip seal 14 effects the sealing of the chamber cover 16 to the basic jar assembly 10. It is to this chamber cover 16 and its incorporated funnel and filler cap, 50 and 18 respectively, to which the major attention is to be directed. The chamber cover is otherwise conventional, having inlet and outlet tubes 54 and 56 respectively, one of which has heretofore been used as the filler orifice. O-ring 48 is of such a dimension as to seal when inserted in to the small part of the funnel.

Figure 2:
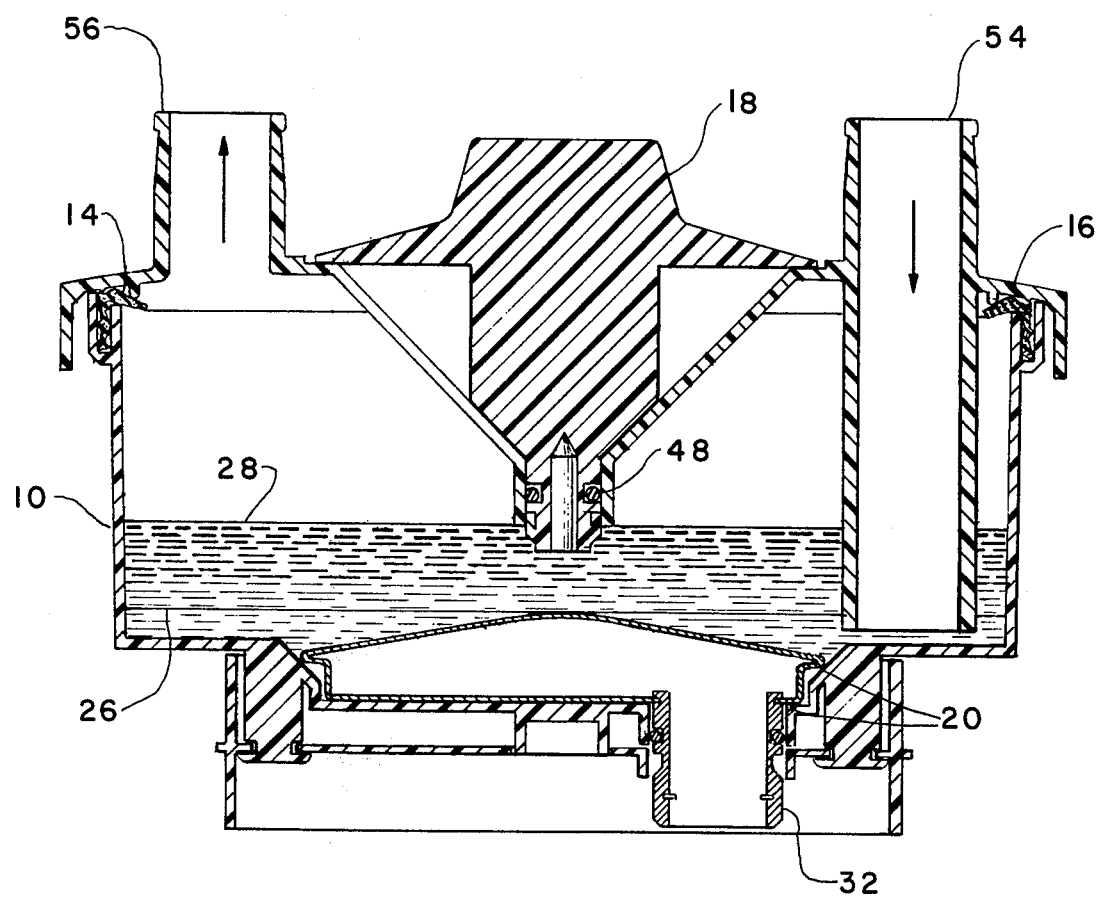
FIG. 2 is a cross-section of the assembled humidifier system.

FIG. 2 shows the assembled unit in cross-section and further illustrates the high and low fluid level marks, 28 and 26 respectively. O-ring 48 is shown as assembled to filler cap 18 and sealingly inserted into the funnel. Lip seal 14 is shown as pressed down by chamber cover 16. Gas inlet and outlet tubes are respectively 54 and 56. The shroud 32 is provided for the connector assembly to conduct electrical power to the heater which has hermetic seals 20.

Figure 3:
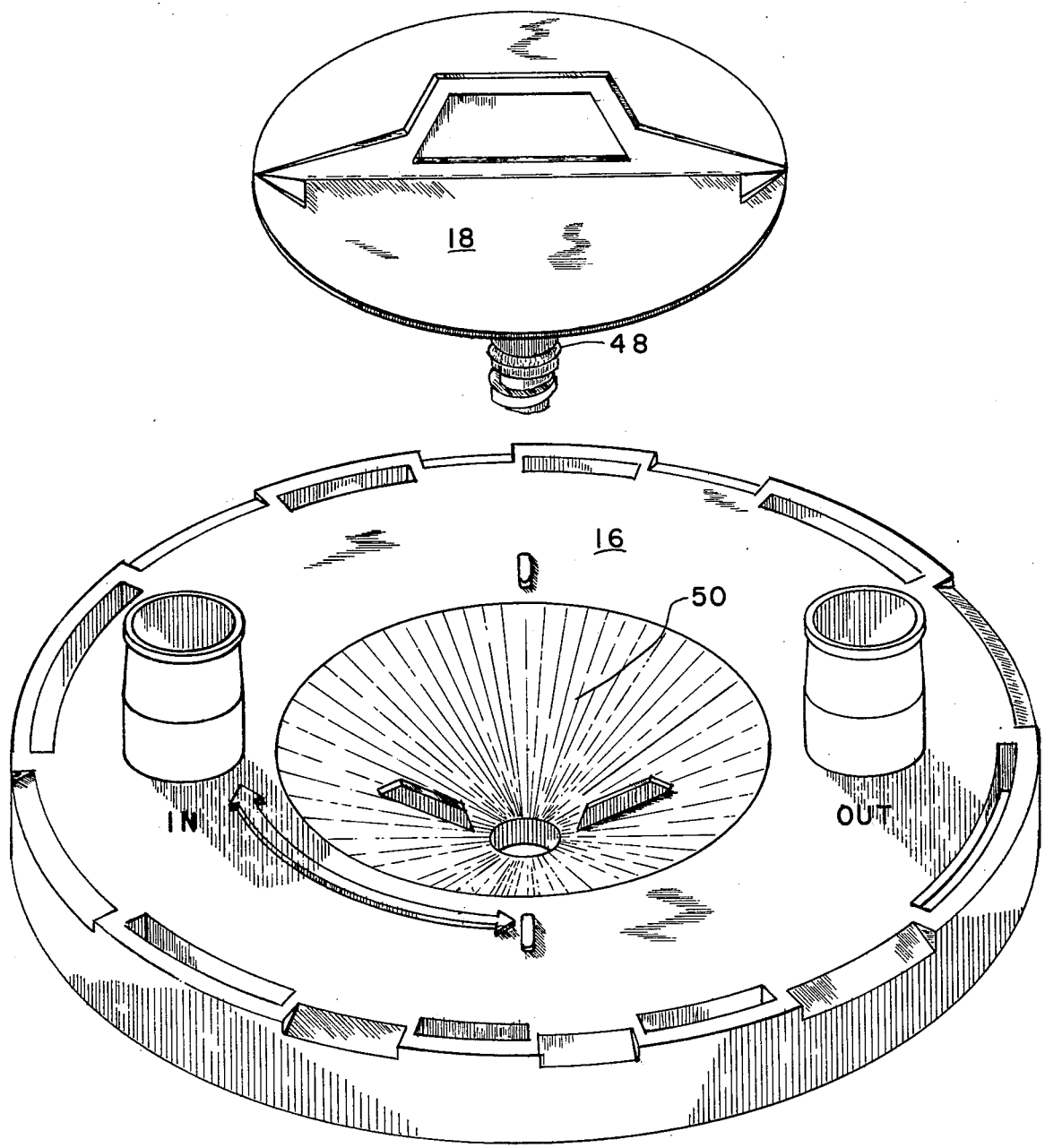
FIG. 3 is a perspective drawing showing the funnel incorporated into the chamber cover with the filler cap removed as it would be for adding fluid to the system.

Referring now to FIG. 3, the funnel 50 is seen from the perspective of one about to add fluid to the system. It will be noted that the funnel 50 has been formed as an integral part of chamber cover 16. Filler cap 18 with its sealing O-ring 48 has been removed to permit access to the funnel so as to add fluid to the unit after which the filler cap will be replaced to prevent entry of contaminants to the system.

Thus there has been described a sealable humidifier refill means that allows addition of fluid to the system of a humidifier without the necessity to remove attached tubing from either the inlet or outlet tubes of the chamber cover. Great improvements in ease of operation, safety, reliability and flexibility have been provided through the novel advantages of the invention.

It is pointed out that although the present invention has been shown and described with reference to particular embodiment, nevertheless various changes and modifications obvious to one skilled in the art to which the invention pertains are deemed to lie within the purview of the invention.

What is claimed and desired to be secured by Letters Patent of the United States is:

1. A cover assembly for a humidifier chamber of the type used with a medical respirator, said assembly comprising:
    a humidifier chamber cover having a substantially horizontal wall with inlet and outlet tubes extending perpendicularly therefrom, said horizontal wall defining a humidifier interior surface
    chamber filling means in the form of a funnel independent of said inlet and outlet tubes and integrally molded into said chamber cover, said funnel substantially having a conical mouth extending through said cover and downwardly from said interior surface, and a cylindrical outlet conduit means extending downwardly from said conical mouth, said outlet conduit means dimensioned so as to have a lower end which terminates at a preselected fluid level when said cover is attached to said humidifier chamber, thereby providing a visual indication of said fluid level through said conical mouth; and a removable filler cap sealingly closing said funnel.

2. The cover assembly of claim 1, wherein said removable filler cap includes:
    a disk-like cover portion dimensioned to cover said mouth;
    a cylindrical shank portion insertable into said cylindrical outlet conduit means of said funnel;
    sealing means on said cylindrical shank portion for sealing said cylindrical outlet conduit means of said funnel; and
    a handle incorporated onto said disk-like cover portion to facilitate insertion to and removal from said funnel.

* * * * *